United States Patent
Takeuchi et al.

(10) Patent No.: US 6,613,246 B2
(45) Date of Patent: Sep. 2, 2003

(54) POLYMERIZABLE LIQUID CRYSTAL COMPOUND HAVING AMIDO BOND BETWEEN TWO CYCLIC GROUPS

(75) Inventors: Hiroshi Takeuchi, Kanagawa (JP); Ken Kawata, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 111 days.

(21) Appl. No.: 09/803,020

(22) Filed: Mar. 12, 2001

(65) Prior Publication Data

US 2001/0035520 A1 Nov. 1, 2001

(30) Foreign Application Priority Data

Mar. 13, 2000 (JP) ........................................ 2000-068479

(51) Int. Cl.[7] ............................................. C09K 19/20
(52) U.S. Cl. ............................ 252/299.67; 252/299.64; 252/299.68; 252/299.01; 428/1
(58) Field of Search ................. 252/299.01; 349/86–88, 349/92–94, 106, 12, 188; 428/1

(56) References Cited

U.S. PATENT DOCUMENTS 5,729,319 A * 3/1998 Inou et al. .................. 349/156
5,769,393 A * 6/1998 Kobayashi et al. ..... 252/299.01

* cited by examiner

Primary Examiner—Mark F. Huff
Assistant Examiner—Jennifer R. Sadule
(74) Attorney, Agent, or Firm—Burns, Doane, Swecker & Mathis, LLP

(57) ABSTRACT

A polymerizable liquid crystal compound is represented by the formula (I):

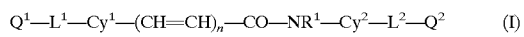

in which each of $Q^1$ and $Q^2$ independently is a polymerizable group; each of $L^1$ and $L^2$ independently is a divalent linking group; each of $Cy^1$ and $Cy^2$ independently is a divalent cyclic group; $R^1$ is hydrogen or an alkyl group having 1 to 7 carbon atoms; and n is 0 or 1.

20 Claims, No Drawings

POLYMERIZABLE LIQUID CRYSTAL COMPOUND HAVING AMIDO BOND BETWEEN TWO CYCLIC GROUPS

FIELD OF THE INVENTION

The present invention relates to a polymerizable liquid crystal compound having an amido bond between two cyclic groups. The invention also relates to an optically anisotropic element prepared from the compound.

BACKGROUND OF THE INVENTION

Alignment of molecules of a polymerizable liquid crystal compound can be fixed by polymerization after the molecules are aligned. The polymerizable liquid crystal compounds are described in U.S. Pat. Nos. 4,683,327, 4,983,479, 5,622,648 and 5,770,107; and W.O. Patent Nos. 95/22586 and 97/00600.

An optically anisotropic polymer prepared by the polymerization can be used as an optically anisotropic element. For example, a polarizing prism made of the optically anisotropic polymer is described in European Patent No. 428213. Further, an optical compensatory sheet (for liquid crystal display of STN mode) made of the optically anisotropic polymer is described in European Patent No. 428881. Furthermore, a cholesteric polarizer made of the optically anisotropic polymer is described in European Patent No. 606940.

SUMMARY OF THE INVENTION

The present inventors have studied polymerizable liquid crystal compounds, and have found that the known compounds have disadvantages in phase transition temperature and optical characteristics. For example, the known compounds often change into isotropic liquid at low temperatures or exhibit liquid phase within narrow temperature ranges. Further, known polymerizable liquid crystal compounds sometimes have small birefringent indexes to be used in an optically anisotropic material (such as an optically anisotropic element).

An object of the present invention is to provide a polymerizable liquid crystal compound having an appropriate phase transition temperature.

Another object of the invention is to provide a polymerizable liquid crystal compound having a large birefringent index.

A further object of the invention is to provide an optically anisotropic element having optical anisotropy, which can be easily produced.

The present invention provides a polymerizable liquid crystal compound represented by the formula (I):

$$Q^1—L^1—Cy^1—(CH=CH)_n—CO—NR^1—Cy^2—L^2—Q^2 \quad (I)$$

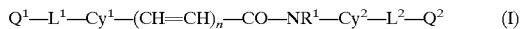

in which each of $Q^1$ and $Q^2$ independently is a polymerizable group; each of $L^1$ and $L^2$ independently is a divalent linking group; each of $Cy^1$ and $Cy^2$ independently is a divalent cyclic group; $R^1$ is hydrogen or an alkyl group having 1 to 7 carbon atoms; and n is 0 or 1.

The invention also provides An optically anisotropic element comprising a transparent support and a liquid crystal layer formed by polymerization of a polymerizable liquid crystal compound, wherein the polymerizable liquid crystal compound is represented by the formula (I).

The present inventors have found that the polymerizable liquid crystal compound represented by the formula (I) changes into isotropic liquid at a high temperature and exhibits liquid phase within a wide temperature range. Further, the compound has a large birefringent index. The compound of the formula (I) has a specific mesogen structure, in which an amide bond (—CO—NR—) is present between two cyclic groups ($Cy^1$ and $Cy^2$), each of which further links to a polymerizable group (Q) through a linking group (L). Because of the specific mesogen structure, the compound can exhibit liquid phase within a wide temperature range and has a large birefringent index.

Since the polymerizable liquid crystal compound gives liquid phase within a wide temperature range, alignment of the liquid crystal molecules can be easily maintained during polymerization reaction. Accordingly, an optically anisotropic element can be easily prepared by polymerization reaction of the polymerizable liquid crystal compound represented by the formula (I).

Since the compound of the formula (I) has a large birefringent index, an optically anisotropic element having high anisotropy can be obtained.

DETAILED DESCRIPTION OF THE INVENTION

The polymerizable liquid crystal compound of the invention is represented by the formula (I).

$$Q^1—L^1—Cy^1—(CH=CH)_n—CO—NR^1—Cy^2—L^2—Q^2. \quad (I)$$

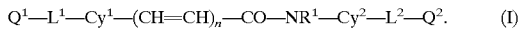

In the formula (I), each of $Q^1$ and $Q^2$ independently is a polymerizable group. The polymerizable group is preferably polymerized by addition (including ring-opening) or condensation polymerization reaction. In other words, the polymerizable group is preferably a functional group which can be subjected to addition or condensation polymerization reaction.

Examples of the polymerizable groups (Q) are shown below.

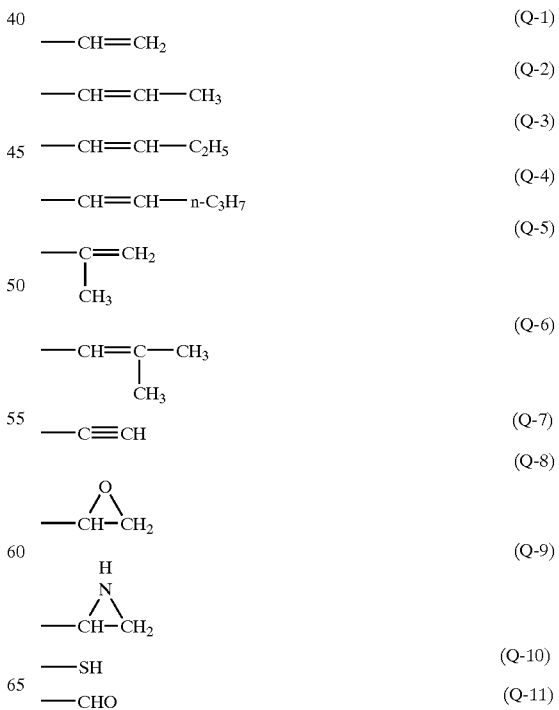

-continued

—OH (Q-12)

—CO$_2$H (Q-13)

—N=C=O (Q-14)

—NH$_2$ (Q-15)

—SO$_3$H (Q-16)

—N=C=S (Q-17)

The polymerizable group (Q$^1$ or Q$^2$) preferably is an unsaturated polymerizable group (Q-1 to Q-7), an epoxy group (Q-8) or an aziridinyl group (Q-9), more preferably is an unsaturated polymerizable group, and most preferably is an ethylenically unsaturated group (Q-1 to Q-6).

In the formula (I), each of L$^1$ and L$^2$ independently is a divalent linking group. The divalent linking group is preferably selected from the group consisting of —O—, —S—, —CO—, —NR$^2$—, a divalent chain group, a divalent cyclic group and a combination thereof. R$^2$ is hydrogen or an alkyl group having 1 to 7 carbon atoms.

Examples of the combined divalent linking group are shown below. In the examples, the left side is attached to Q (Q$^1$ or Q$^2$), and the right side is attached to Cy (Cy$^1$ or Cy$^2$). CH means a divalent chain group, and CY means a divalent cyclic group.

L1: —CO—O—CH—O—
L2: —CO—O—CH—O—CY—CO—O—
L3: —CO—O—CH—O—CY—O—CO—
L4: —CO—O—CH—O—CY—CH—
L5: —CO—O—CH—O—CY—
L6: —CO—O—CH—O—CY—CH—CO—O—
L7: —CO—O—CH—O—CY—O—CO—CH—

The divalent chain groups (CH) include an alkylene group, a substituted alkylene group, an alkenylene group, a substituted alkenylene group, an alkynylene group or a substituted alkynylene group. An alkylene group, a substituted alkylene group, an alkenylene group and a substituted alkenylene group are preferred, and an alkylene group and an alkenylene group are more preferred.

The alkylene group may have a branched structure. The alkylene group preferably has 1 to 12 carbon atoms, more preferably has 2 to 10 carbon atoms, and most preferably has 3 to 8 carbon atoms.

The alkylene moiety of the substituted alkylene group is the same as the above-described alkylene group. Examples of the substituent groups of the substituted alkylene groups include a halogen atom.

The alkenylene group may have a branched structure. The alkenylene group preferably has 2 to 12 carbon atoms, more preferably has 2 to 8 carbon atoms, and most preferably has 2 to 4 carbon atoms.

The alkenylene moiety of the substituted alkenylene group is the same as the above-described alkenylene group. Examples of the substituent groups of the substituted alkylene groups include a halogen atom.

The alkynylene group may have a branched structure. The alkynylene group preferably has 2 to 12 carbon atoms, more preferably has 2 to 8 carbon atoms, and most preferably has 2 to 4 carbon atoms.

The alkynylene moiety of the substituted alkynylene group is the same as the above described alkynylene group. Examples of the substituent groups of the substituted alkylene groups include a halogen atom.

The definition and the examples of the divalent cyclic groups (CY) are the same as those for Cy$^1$ and Cy$^2$ described below.

R$^2$ preferably is hydrogen or an alkyl group having 1 to 4 carbon atoms, more preferably is hydrogen or an alkyl group having 1 or 2 carbon atoms, and most preferably is hydrogen.

L$^2$ is preferably —O—CO—(CH=CH)$_m$—Cy$^3$—L$^3$— or —(CH=CH)$_m$—CO—O—Cy$^3$—L$^3$—, in which m is 0 or 3, Cy$^3$ is a divalent cyclic group and L$^3$ is a divalent linking group.

The above m is preferably 0 rather than 1.

The definition and the examples of the divalent cyclic group are the same as those for Cy$^1$ and Cy$^2$ described below.

L$^3$ preferably is a divalent linking group selected from the group consisting of —O—, —S—, —CO—, —NR$^2$—, a divalent chain group and a combination thereof. R$^2$ is hydrogen or an alkyl group having 1 to 7 carbon atoms. R$^2$ preferably is hydrogen or an alkyl group having 1 to 4 carbon atoms, more preferably is hydrogen or an alkyl group having 1 or 2 carbon atoms, and most preferably is hydrogen.

L$^3$ most preferably is —O—CH—O—CO—, in which CH is a divalent chain group.

The polymerizable liquid crystal compound represented by the formula (I) preferably have three divalent cyclic groups (Cy$^1$, Cy$^2$ and Cy$^3$).

In the formula (I), each of Cy$^1$ and Cy$^2$ independently is a divalent cyclic group.

The ring in the cyclic group preferably is a five-membered, six-membered or seven membered ring, more preferably is a five-membered or six-membered ring, and most preferably is a six-membered ring.

The ring can be condensed with another ring. However, a monocyclic ring is preferred to a condensed ring.

The ring in the cyclic group can be an aromatic ring, an aliphatic ring or a heterocyclic ring.

Examples of the aromatic rings include benzene ring and naphthalene ring. Examples of the aliphatic ring include cyclohexane ring. Examples of the heterocyclic ring include pyridine ring and pyrimidine ring.

A preferred cyclic group having a benzene ring is 1,4-phenylene. A preferred cyclic groups having a naphthalene ring include naphthalene-1,5-diyl and naphthalene-2,6-diyl. A preferred cyclic group having a cyclohexane ring is 1,4-cyclohexylene. A preferred cyclic group having a pyridine ring is pyridine-2,5-diyl. A preferred cyclic group having a pyrimidine ring is pyrimidine-2,5-diyl.

The cyclic group most preferably is 1,4-phenylene or 1,4-cyclohexylene.

The cyclic group can have a substituent group. Examples of the substituent group include a halogen atom, cyano, nitro, an alkyl group having 1 to 5 carbon atoms, a halogen-substituted alkyl group having 1 to 5 carbon atoms, an alkoxy group having 1 to 5 carbon atoms, an alkylthio group having 1 to 5 carbon atoms, an acyl group having 1 to 5 carbon atoms, an acyloxy group having 2 to 6 carbon atoms, an alkoxycarbonyl group having 2 to 6 carbon atoms, carbamoyl, an alkyl carbamoyl group having 2 to 6 carbon atoms and an amido group having 2 to 6 carbon atoms.

In the formula (I), R$^1$ is hydrogen or an alkyl group having 1 to 7 carbon atoms. R$^1$ preferably is hydrogen or an alkyl group having 1 to 4 carbon atoms, more preferably is hydrogen or an alkyl group having 1 to 2 carbon atoms, and most preferably is hydrogen.

In the formula (I), n is an integer of 0 or 1. Preferably, n is 0 rather than 1.

The polymerizable liquid crystal compound is preferably represented by the formula (IIa) or (IIb). The compound of the formula (IIa) is more preferred.

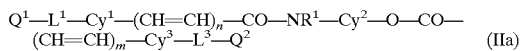
(IIa)

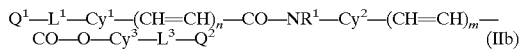
(IIb)

In the formulas (IIa) and (IIb), each of $Q^1$ and $Q^2$ independently is a polymerizable group. The definition and the examples of the polymerizable group are the same as those described for the formula (I).

In the formulas (IIa) and (IIb), each of $L^1$ and $L^3$ independently is a divalent linking group. The divalent linking group is preferably selected from the group consisting of —O—, —S—, —CO—, —NR$^2$—, a divalent chain group and a combination thereof. $R^2$ is hydrogen or an alkyl group having 1 to 7 carbon atoms. $R^2$ preferably is hydrogen or an alkyl group having 1 to 4 carbon atoms, more preferably is hydrogen or an alkyl group having 1 or 2 carbon atoms, and most preferably is hydrogen.

$L^1$ preferably is —CO—O—CH—O—, in which CH is a divalent chain group. $L^3$ preferably is —O—CH—O—CO—, in which CH is a divalent chain group.

The definition and the examples of the divalent chain group (CH) are the same as those described for the formula (I).

In the formulas (IIa) and (IIb), each of $Cy^1$, $Cy^2$ and $Cy^3$ independently is a divalent cyclic group.

The definition and the examples of the divalent cyclic group are the same as those described for the formula (I).

In the formulas (IIa) and (IIb), $R^1$ is hydrogen or an alkyl group having 1 to 7 carbon atoms. $R^1$ preferably is hydrogen or an alkyl group having 1 to 4 carbon atoms, more preferably is hydrogen or an alkyl group having 1 or 2 carbon atoms, and most preferably is hydrogen.

In the formulas (IIa) and (IIb), each of m and n is independently an integer of 0 or 1. Preferably, each of m and n is 0 rather than 1.

The polymerizable liquid crystal compound is further preferably represented by the formula (IIIa) or (IIIb). The compound of the formula (IIIa) is furthermore preferred.

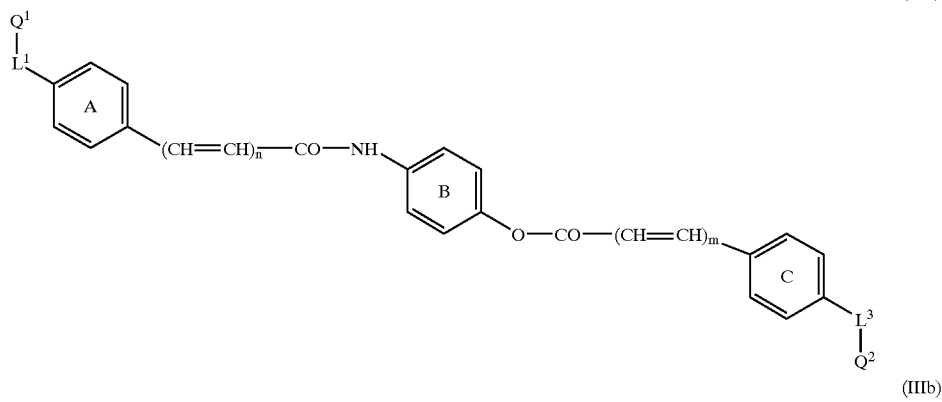
(IIIa)

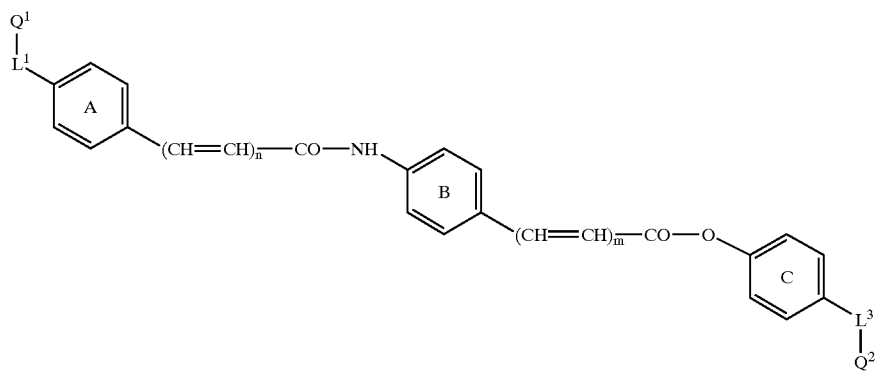
(IIIb)

In the formulas (IIIa) and (IIIb), each of $Q^1$ and $Q^2$ independently is a polymerizable group. The definition and the examples of the polymerizable group are the same as those described for the formula (I).

In the formulas (IIIa) and (IIIb), each of $L^1$ and $L^3$ independently is a divalent linking group. The divalent linking group is preferably selected from the group consisting of —O—, —S—, —CO—, NR$^2$—, a divalent chain group and a combination thereof. $R^2$ is hydrogen or an alkyl group having 1 to 7 carbon atoms. $R^2$ preferably is hydrogen or an alkyl group having 1 to 4 carbon atoms, more preferably is hydrogen or an alkyl group having 1 or 2 carbon atoms, and most preferably is hydrogen.

$L^1$ preferably is —CO—O—CH—O—, in which CH is a divalent chain group. $L^3$ preferably is —O—CH—O—CO—, in which CH is a divalent chain group.

The definition and the examples of the divalent chain group (CH) are the same as those described for the formula (I).

In the formulas (IIIa) and (IIIb), each of m and n is independently an integer of 0 or 1. Preferably, each of m and n is 0 rather than 1.

In the formulas (IIIa) and (IIIb), the benzene rings A and B can have substituent groups. Examples of the substituent group are the same as those of the divalent cyclic group in the formula (I).

Examples of the polymerizable liquid crystal compounds represented by the formula (I) are shown below.

(I-1)

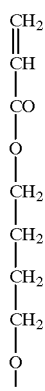

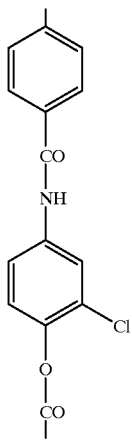

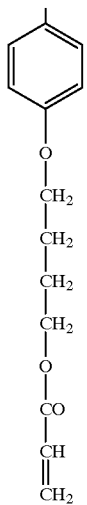

(I-2)

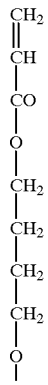

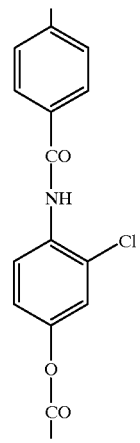

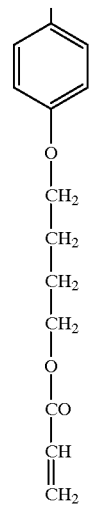

(I-3)
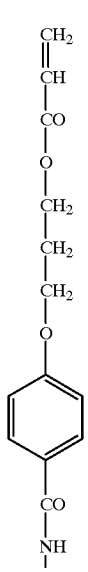
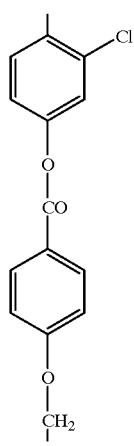
(I-4)
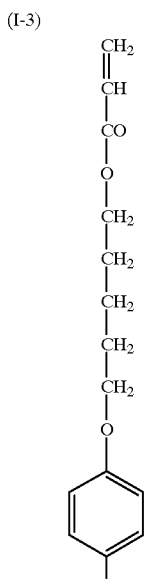
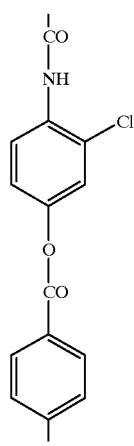
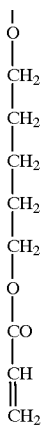

(I-5)
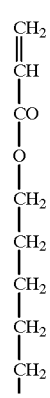
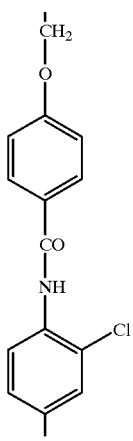
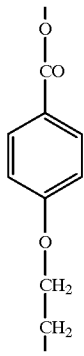
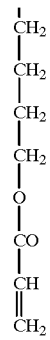
(I-6)
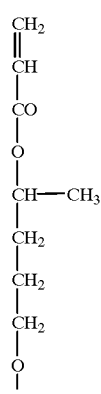
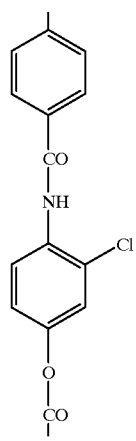
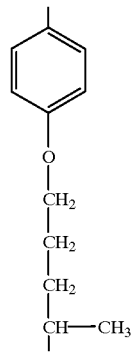

(I-7)
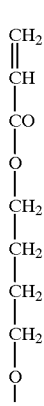
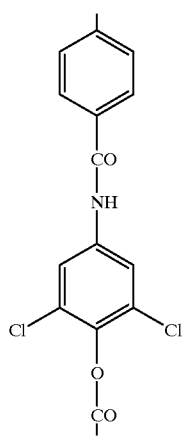
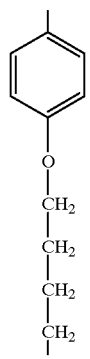
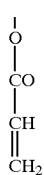
(I-8)
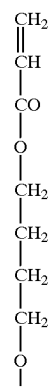
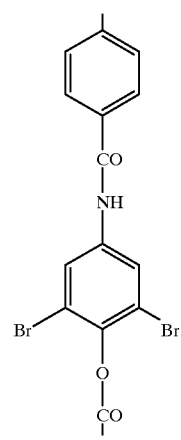
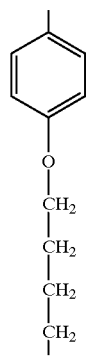
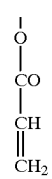

(I-9)
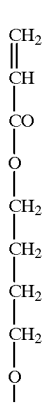
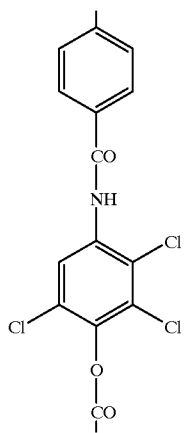
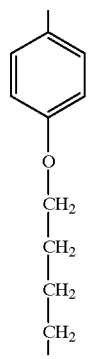
(I-10)
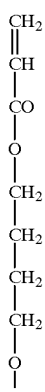
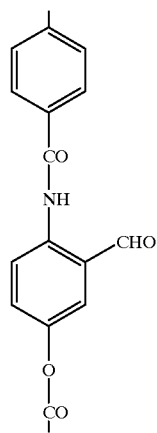
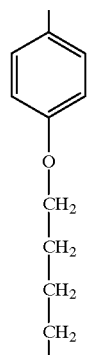

(I-11)
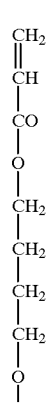
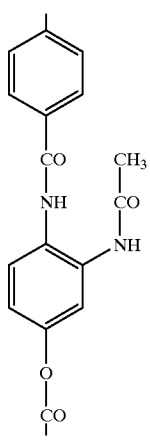
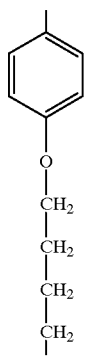
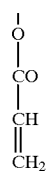
(I-12)
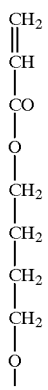
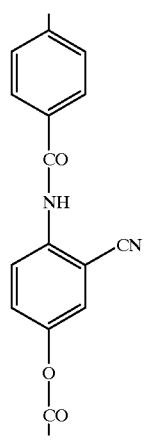
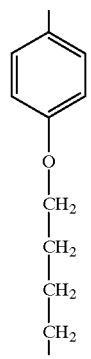

(I-13)
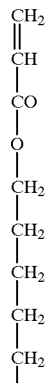
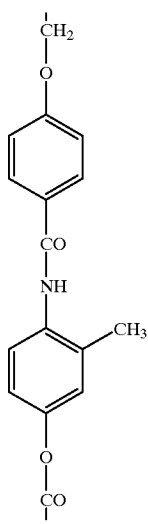
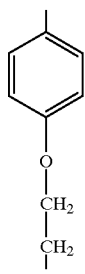
(I-14)
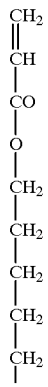
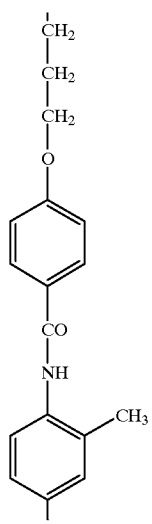
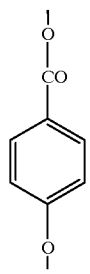
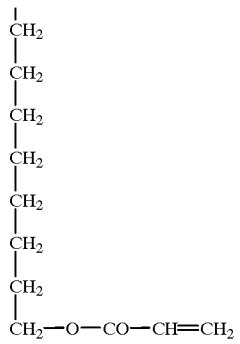

(I-15)
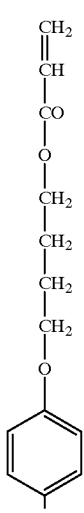
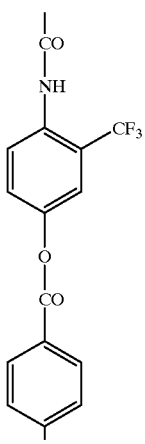
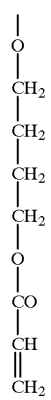
(I-16)
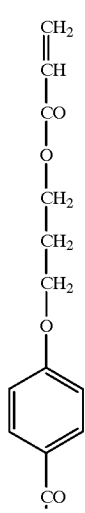
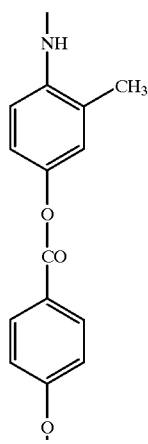
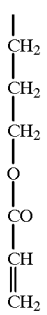

(I-17)
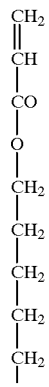
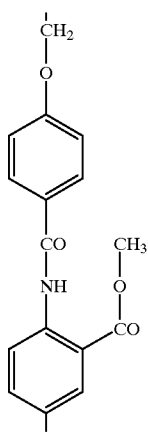
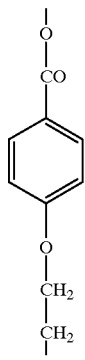
(I-18)
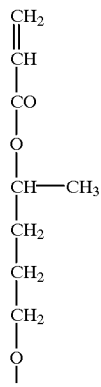
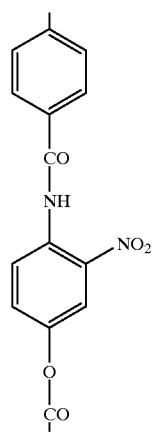
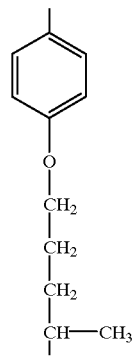

(I-19)
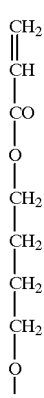
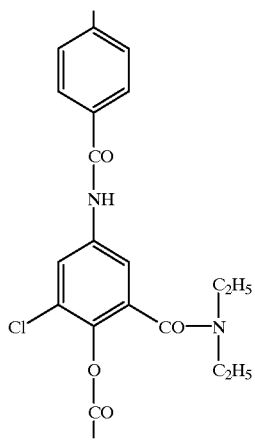
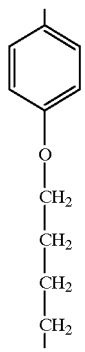
(I-20)
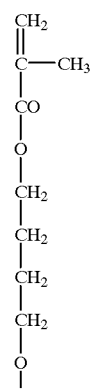
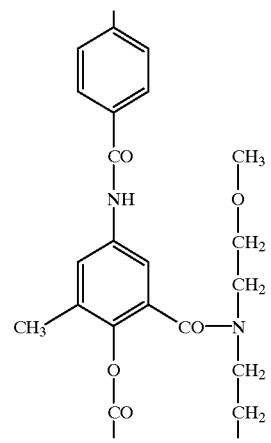
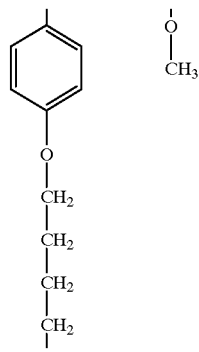
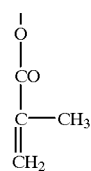

(I-21) 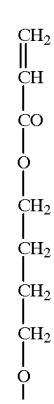 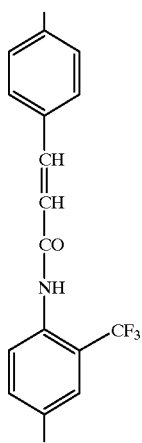 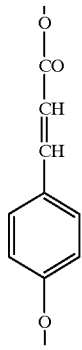 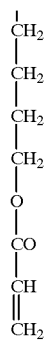
(I-22) 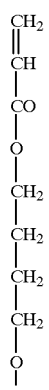 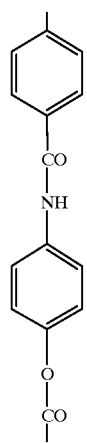 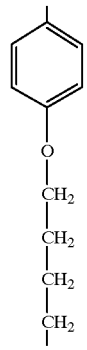 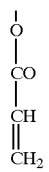

-continued

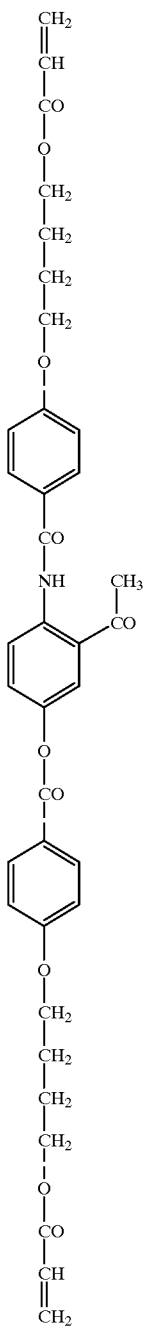

(I-23)

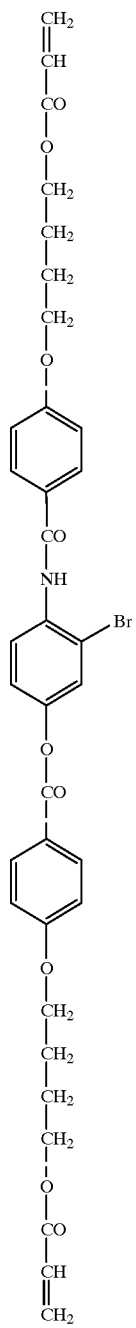

(I-24)

The polymerizable liquid crystal compound represented by the formula (I) can be synthesized by referring known methods (for example, described in Methoden der Organischen Chemie [Houben-Weyl], Some Specific Methods [Thieme-Verlag, Stuttgart], Jikken Kagaku Koza and Shin-Jikken Kagaku Koza). The compounds can also be synthesized by referring to the descriptions of U.S. Pat. Nos. 4,683,327, 4,983,479, 5,622,648 and 5,770,107; W.O. Patent Nos. 95/22586, 97/00600 and 98/47979; and British Patent No. 2297549.

[Optically Anisotropic Element]

An optically anisotropic element can be prepared by coating an orientation layer with a liquid crystal composition (coating solution) comprising the polymerizable liquid crystal compound represented by the formula (I) and then polymerizing the molecules of the liquid crystal compound to form a liquid crystal layer.

The composition can be applied according to a conventional coating method such as an extrusion coating method, a direct gravure coating method, a reverse gravure coating method, a die coating method or a bar coating method.

The liquid crystal molecules are fixed with the alignment maintained. The liquid crystal molecules are fixed by a polymerization reaction of the polymerizable groups (Q) in the molecules. The polymerization reaction can be classified into a thermal reaction using a thermal polymerization initiator and a photo reaction using a photo polymerization initiator. A photo polymerization reaction is preferred.

Examples of the photo polymerization initiators include α-carbonyl compounds (described in U.S. Pat. Nos. 2,367, 661, 2,367,670), acyloin ethers (described in U.S. Pat. No. 2,448,828), α-hydrocarbon substituted acyloin compounds (described in U.S. Pat. No. 2,722,512), polycyclic quinone compounds (described in U.S. Pat. Nos. 2,951,758, 3,046, 127), combinations of triarylimidazoles and p-aminophenyl ketones (described in U.S. Pat. No. 3,549,367), acridine or phenazine compounds (described in Japanese Patent Provisional Publication No. 60(1985)-105667 and U.S. Pat. No. 4,239,850) and oxadiazole compounds (described in U.S. Pat. No. 4,212,970).

The amount of the photo polymerization initiator is preferably in the range of 0.01 to 20 wt. %, and more preferably in the range of 0.5 to 5 wt. % based on the solid content of the coating solution.

The light irradiation for the photo polymerization may be conducted with an ultraviolet ray.

The exposure energy is preferably in the range of 20 to 50,000 mJ/cm$^2$, and more preferably in the range of 100 to 800 mJ/cm$^2$. The light irradiation can be conducted with the layer heated to accelerate the photo polymerization reaction.

The liquid crystal layer has a thickness preferably in the range of 0.1 to 50 μm, more preferably 1 to 30 μm, and most preferably in the range of 5 to 20 μm.

[Orientation Layer]

The orientation layer can be formed by rubbing treatment of an organic compound (preferably a polymer), oblique evaporation of an inorganic compound, formation of a micro groove layer, or stimulation of an organic compound (e.g., (ω-tricosanoic acid, dioctadecylmethylammonium chloride, methyl stearate) according to a Langmuir-Blodgett method. Further, the aligning function of the orientation layer can be activated by applying an electric or magnetic field to the layer or irradiating the layer with light. The orientation layer is preferably formed by rubbing a polymer. The rubbing treatment can be conducted by rubbing a layer containing the aforementioned polymer with paper or cloth several times along a certain direction.

The polymer used for the orientation layer is selected according to aimed alignment (particularly, aimed average inclined angle) of the liquid crystal molecules.

For horizontally aligning the liquid crystal molecules (at an average inclined angle of 0 to 50°), a polymer that does not reduce the surface energy of the orientation layer (i.e., a polymer usually used for an orientation layer) is used.

In contrast, for vertically aligning the liquid crystal molecules (at an average inclined angle of 50 to 90°), a polymer that reduces the surface energy of the orientation layer is used. That polymer preferably has a hydrocarbon group of 10 to 100 carbon atoms at the side chain.

Concrete examples of the polymer are described in various publications concerning liquid crystal cells or optical compensatory sheets.

The orientation layer has a thickness of preferably 0.01 to 5 μm, more preferably 0.05 to 1 μm.

After the liquid crystal molecules are aligned with the orientation layer, the liquid crystal layer can be transferred onto the transparent support. The aligned and fixed liquid crystal molecules can keep the alignment without the orientation layer.

For aligning the molecules at an average inclined angle less than 5°, neither rubbing treatment nor the orientation layer is needed. However, an orientation layer (described in Japanese Patent Provisional Publication No. 9(1997)-152509) that forms chemical bonding at the interface between the liquid crystal molecules and the layer may be provided to improve the adhesion. In that case, rubbing treatment is unnecessary.

[Transparent Support]

A transparent support is a glass plate or a polymer film, preferably a polymer film. The term "transparent" here means that light transmittance is not less than 80%.

The transparent support has a thickness preferably in the range of 10 to 500 μm, and more preferably in the range of 50 to 200 μm.

The transparent support can be subjected to a surface treatment (e.g., glow discharge treatment, corona discharge treatment, ultraviolet (UV) treatment, flame treatment) to improve adhesion to a layer formed on the support (e.g., adhesive layer, orientation layer, liquid crystal layer).

An ultraviolet absorber may be incorporated in the transparent support.

An adhesive layer (undercoating layer) can be provided on the transparent support. Japanese Patent Provisional Publication 7(1995)-333433 describes the adhesive layer. The thickness of the adhesive layer is in the range of preferably 0.1 to 2 μm, more preferably 0.2 to 1 μm.

[Use of Optically Anisotropic Element]

The optically anisotropic element of the invention can be used as an optical compensatory sheet for liquid crystal displays of various modes. Examples of the display modes include TN (twisted nematic) mode, IPS (in-plane switching) mode, FLC (ferroelectric liquid crystal) mode, OCB (optically compensatory bend) mode, STN (super twisted nematic) mode, VA (vertically aligned) mode, GH (guest-host) mode and HAN (hybrid aligned nematic) mode.

The optically anisotropic element can be also used as a polarizing prism (described in European Patent No. 428213).

Further, the element can be used as a cholesteric polarizer (described in European Patent No. 606940).

EXAMPLE 1

Synthesis of Polymerizable Liquid Crystal Compound (I-1)

The polymerizable liquid crystal compound (I-1) was synthesized according to the following scheme. The compounds (a) to (d) can be synthesized according to a known method by referring to the above-described references.

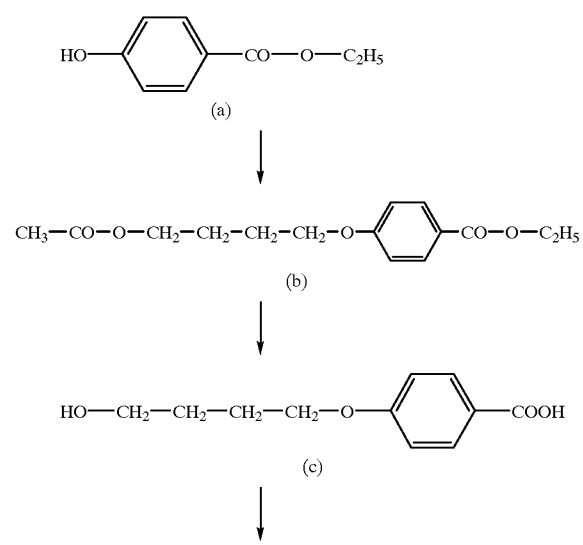

-continued

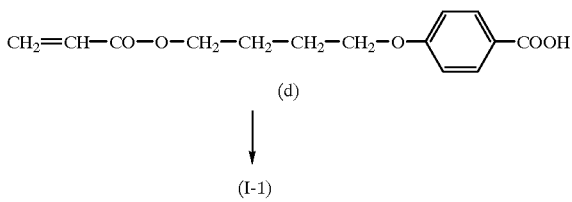

(d)

↓

(I-1)

In 20 ml of tetrahydrofuran, 1.54 ml of methane sulfonylchloride was dissolved and cooled to −10° C. To the solution, a solution in which 5.5 g of the compound (d) and 3.75 ml of N-ethyldiisopropylamine were dissolved in 20 ml of tetrahydrofuran was dropwise added with the liquid temperature kept below 5° C. The mixture was stirred at room temperature for 30 minutes, and cooled again. After 3.75 ml of N-ethyldiisopropylamine and 0.3 g of 4-N,N-dimethyl-aminopyridine were added, a solution in which 1.43 g of 4-amino-2-chlorophenol was dissolved in 10 ml of tetrahydrofuran was dropwise added with the liquid temperature kept below 5° C. The mixture was stirred at room temperature for 3 hours, and poured into 300 ml of water. The reaction mixture was extracted with 200 ml of ethyl acetate, and the organic phase was collected and washed twice with water. After drying with sodium sulfate, the liquid was concentrated under reduced pressure. The formed crude product was recrystallized from ethyl acetate and n-hexane to obtain 2.3 g of the polymerizable liquid crystal compound (I-1). The structure of the obtained compound was confirmed by $^1$H-NMR and mass spectrometry. The polymerizable liquid crystal compound (I-1) exhibited monotropic phases. The phase transition temperatures were (crystal phase→) 127° C. (→isotropic liquid), (isotropic liquid→) 124° C. (→nematic phase→) and 105° C. (→crystal phase).

EXAMPLE 2

Synthesis of Polymerizable Liquid Crystal Compound (I-24)

In 20 ml of tetrahydrofuran, 1.54 ml of methane sulfonylchloride was dissolved and cooled to −10° C. To the solution, a solution in which 5.5 g of the compound (d) used in Example 1 and 3.75 ml of N-ethyldiisopropylamine were dissolved in 20 ml of tetrahydrofuran was dropwise added with the liquid temperature kept below 5° C. The mixture was stirred at room temperature for 30 minutes, and cooled again. After 3.75 ml of N-ethyldiisopropylamine and 0.3 g of 4-N,N-dimethylaminopyridine were added, a solution in which 1.63 g of 4-amino-3-bromophenol was dissolved in 10 ml of tetrahydrofuran was dropwise added with the liquid temperature kept below 5° C. The mixture was stirred at room temperature for 3 hours, and poured into 300 ml of water. The reaction mixture was extracted with 200 ml of ethyl acetate, and the organic phase was collected and washed twice with water. After drying with sodium sulfate, the liquid was concentrated under reduced pressure. The formed crude product was recrystallized from ethyl acetate and n-hexane to obtain 2.7 g of the polymerizable liquid crystal compound (I-24). The structure of the obtained compound was confirmed by $^1$H-NMR and mass spectrometry. The polymerizable liquid crystal compound (I-24) exhibited enantiotropic phase. The phase transition temperatures were (crystal phase→) 82° C. (→nematic phase→) and 137° C. (→isotropic liquid).

EXAMPLE 3

The polymerizable liquid crystal compounds (I-2), (I-3), (I-5), (I-11), (I-12), (I-13), (I-15), (I-21) and (I-23) were prepared In the same manner as Example 1 or 2.

The compounds (I-1), (I-2), (I-3), (I-5), (I-11), (I-12), (I-13), (I-15), (I-21), (I-23) and (I-24) were measured with respect to phase transition temperatures and birefringent indexes.

Known polymerizable liquid crystal compounds (Ref-1, described in Advanced Materials, vol. 5, no. 2, pp. 108) and (Ref-2, described in U.S. Pat. No. 5,770,107) were also measured with respect to phase transition temperatures and the birefringent indexes.

The birefringence was measured by using an Abbe's refractometer according to a known method (described in Makromol. Chem., vol.190, pp.2255). The birefringence was measured at the temperature of 10° C. lower than the phase transition temperature of isotropic liquid.

The results are set forth in Table 1.

TABLE 1

| Polymerizable liquid crystal compound | Phase transition temperature | | Birefringence (Δn) |
|---|---|---|---|
| | Crystal phase → nematic phase | Nematic phase → isotropic liquid | |
| I-1 | 105° C. | 124° C. | 0.128 |
| I-2 | 89° C. | 152° C. | 0.126 |
| I-3 | 89° C. | 136° C. | 0.123 |
| I-5 | 80° C. | 155° C. | 0.129 |
| I-11 | — | 130° C. | 0.122 |
| I-12 | 127° C. | 141° C. | 0.121 |
| I-13 | 88° C. | 148° C. | 0.125 |
| I-15 | 92° C. | 106° C. | 0.123 |
| I-21 | 110° C. | 166° C. | 0.209 |
| I-23 | 93° C. | 123° C. | 0.122 |
| I-24 | 82° C. | 137° C. | 0.125 |
| Ref-1 | 100° C. | 109° C. | 0.131 |
| Ref-2 | 97° C. | 176° C. | 0.207 |

(Ref-1)

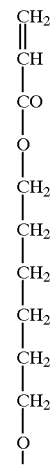

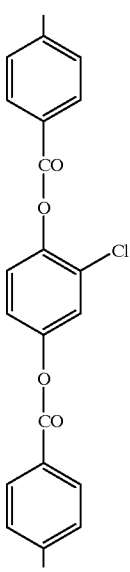
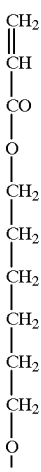

(Ref-2)

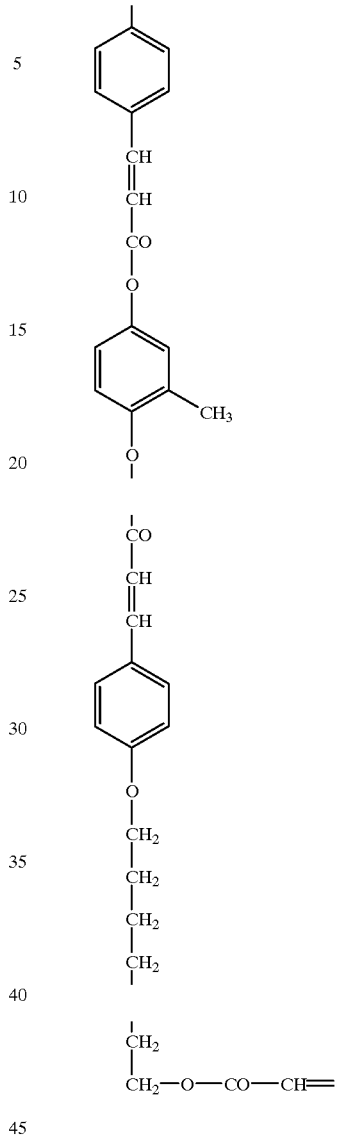

EXAMPLE 4

Preparation of Optically Anisotropic Element

An optically anisotropic element was prepared in the following manner according to Advanced Material, vol. 5, no. 2, pp. 107.

A glass substrate was coated with polyimide (SE-150, Nissan Chemical Co., Ltd.), and subjected to rubbing treatment to form an orientation layer.

In 700 µl of N-methylpyrrolidone, 300 mg of the compound (I-2) and 50 mg of ω,ω-dimethoxy-ω-phenylacetophenone were dissolved. After the prepared solution was dropped on the orientation layer, spin-coating was conducted at 1,000 rpm. The solvent was evaporated by heating at 100° C. for 30 minutes. The surface of the thus-treated glass substrate was observed with a polarizing microscope, to find that the polymerizable liquid crystal molecules were aligned almost parallel to the rubbing direction.

The aligned molecules were then exposed to ultraviolet light from a high pressure mercury lamp under nitrogen gas atmosphere, to polymerize the molecules.

The thus-prepared optically anisotropic element was observed with a polarizing microscope, to find that the alignment had no defect such as domain border or inversion wall.

Two polarizers were arranged in cross-Nicol position, and the optically anisotropic element was placed between them. With the thus-placed element rotated, it was observed whether light passed through the element and the polarizers. As a result, the element alternately gave brightness and darkness every 45 degree.

What is claimed is:

1. A polymerizable liquid crystal compound represented by the formula (IIa) or (IIb):

$$Q^1\text{—}L^1\text{—}Cy^1\text{—}(CH\text{=}CH)_n\text{—}CO\text{—}NR^1\text{—}Cy^2\text{—}O\text{—}CO\text{—}(CH\text{=}CH)_m\text{—}Cy^3\text{—}L^3\text{—}Q^2 \quad \text{(IIa)}$$

$$Q^1\text{—}L^1\text{—}Cy^1\text{—}(CH\text{=}CH)_n\text{—}CO\text{—}NR^1\text{—}Cy^2\text{—}(CH\text{=}CH)_m\text{—}CO\text{—}O\text{—}Cy^3\text{—}L^3\text{—}Q^2 \quad \text{(IIb)}$$

in which each of $Q^1$ and $Q^2$ independently is a polymerizable group; each of $L^1$ and $L^3$ independently is a divalent linking group; each of $Cy^1$, $Cy^2$ and $Cy^3$ independently is a divalent cyclic group; $R^1$ is hydrogen or an alkyl group having 1 to 7 carbon atoms; and each of n and m independently is 0 or 1.

2. The polymerizable liquid crystal compound as defined in claim 1, wherein each of $Q^1$ and $Q^2$ in the formula (IIa) or (IIb) independently is a polymerizable group selected from the group consisting of (Q-1) to (Q-17):

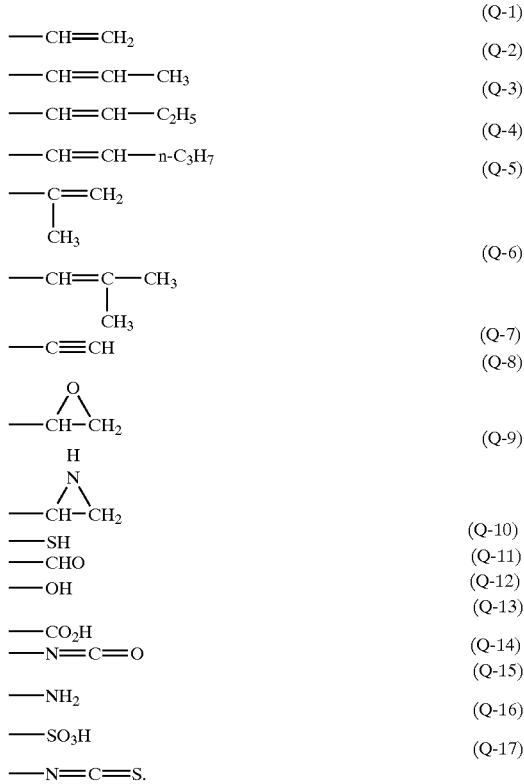

3. The polymerizable liquid crystal compound as defined in claim 1, wherein each of $Q^1$ and $Q^2$ in the formula (IIa) or (IIb) independently is an ethylenically unsaturated polymerizable group.

4. The polymerizable liquid crystal compound as defined in claim 1, wherein each of $L^1$ and $L^3$ in the formula (IIa) or (IIb) independently is a divalent linking group selected from the group consisting of —O—, —S—, —CO—, —NR$^2$—, a divalent chain group, a divalent cyclic group and a combination thereof in which $R^2$ is hydrogen or an alkyl group having 1 to 7 carbon atoms.

5. The polymerizable liquid crystal compound as defined in claim 4, wherein at least one of $L^1$ and $L^3$ is the divalent chain group, and wherein the divalent chain group is an alkylene group, an alkenylene group or an alkynylene group.

6. The polymerizable liquid crystal compound as defined in claim 4, wherein at least one of $L^1$ and $L^3$ is the divalent cyclic group, and wherein the divalent cyclic group has a five-membered, six-membered or seven-membered divalent aromatic, aliphatic or heterocyclic ring, which can be condensed with another ring.

7. The polymerizable liquid crystal compound as defined in claim 1, wherein $L^3$ is —O—CH—O—CO— in the formula (IIa) or (IIb), in which CH is a divalent chain group.

8. The polymerizable liquid crystal compound as defined in claim 1, wherein each of $Cy^1$ and $Cy^2$ in the formula (IIa) or (IIb) independently is 1,4-phenylene or 1,4-cyclohexylene.

9. The polymerizable liquid crystal compound as defined in claim 1, wherein $R^1$ in the formula (IIa) or (IIb) is hydrogen.

10. An optically anisotropic element comprising a transparent support and a liquid crystal layer formed by polymerization of a polymerizable liquid crystal compound, wherein the polymerizable liquid crystal compound is represented by the formula (IIa) or (IIb):

$$Q^1\text{—}L^1\text{—}Cy^1\text{—}(CH\text{=}CH)_n\text{—}CO\text{—}NR^1\text{—}Cy^2\text{—}O\text{—}CO\text{—}(CH\text{=}CH)_m\text{—}Cy^3\text{—}L^3\text{—}Q^2 \quad \text{(IIa)}$$

$$Q^1\text{—}L^1\text{—}Cy^1\text{—}(CH\text{=}CH)_n\text{—}CO\text{—}NR^1\text{—}Cy^2\text{—}(CH\text{=}CH)_m\text{—}CO\text{—}O\text{—}Cy^3\text{—}L^3\text{—}Q^2 \quad \text{(IIb)}$$

in which each of $Q^1$ and $Q^2$ independently is a polymerizable group; each of $L^1$ and $L^3$ independently is a divalent linking group; each of $Cy^1$, $Cy^2$ and $Cy^3$ independently is a divalent linking group; $R^1$ is hydrogen or an alkyl group having 1 to 7 carbon atoms; and each of n and m independently is 0 or 1.

11. The optically anisotropic element as defined in claim 10, wherein each of $Q^1$ and $Q^2$ in the formula (IIa) or (IIb) independently is a polymerizable group selected from the group consisting of (Q-1) to (Q-17):

—CH=CH$_2$ (Q-1)

—CH=CH—CH$_3$ (Q-2)

—CH=CH—C$_2$H$_5$ (Q-3)

—CH=CH—n-C$_3$H$_7$ (Q-4)

—C(CH$_3$)=CH$_2$ (Q-5)

—CH=C(CH$_3$)—CH$_3$ (Q-6)

—C≡CH (Q-7)

-continued

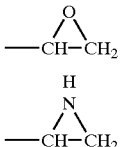

12. The optically anisotropic element as defined in claim 10, wherein each of Q¹ and Q² in the formula (IIa) or (IIb) independently is an ethylenically unsaturated polymerizable group.

13. The optically anisotropic element as defined in claim 10, wherein each of L¹ and L³ in the formula (IIa) or (IIb) independently is a divalent linking group selected from the group consisting of —O—, —S—, —CO—, —NR²—, a divalent chain group, a divalent cyclic group and a combination thereof in which R² is hydrogen or an alkyl group having 1 to 7 carbon atoms.

14. The optically anisotropic element as defined in claim 13, wherein at least one of L¹ and L³ is the divalent chain group, and wherein the divalent chain group is an alkylene group, an alkenylene group or an alkynylene group.

15. The optically anisotropic element as defined in claim 13, wherein at least one of L¹ and L³ is the divalent cyclic group, and wherein the divalent cyclic group has a five-membered, six-membered or seven-membered divalent aromatic, aliphatic or heterocyclic ring, which can be condensed with another ring.

16. The optically anisotropic element as defined in claim 10, wherein L³ is —O—CH—O—CO— in the formula (IIa) or (IIb), in which CH is a divalent chain group.

17. The optically anisotropic element as defined in claim 10, wherein each of Cy¹ and Cy² in the formula (IIa) or (IIb) independently is 1,4-phenylene or 1,4-cyclohexylene.

18. The optically anisotropic element as defined in claim 10, wherein R¹ in the formula (IIa) or (IIb) is hydrogen.

19. A polymerizable liquid crystal compound represented by the formula (IIIa) or (IIIb):

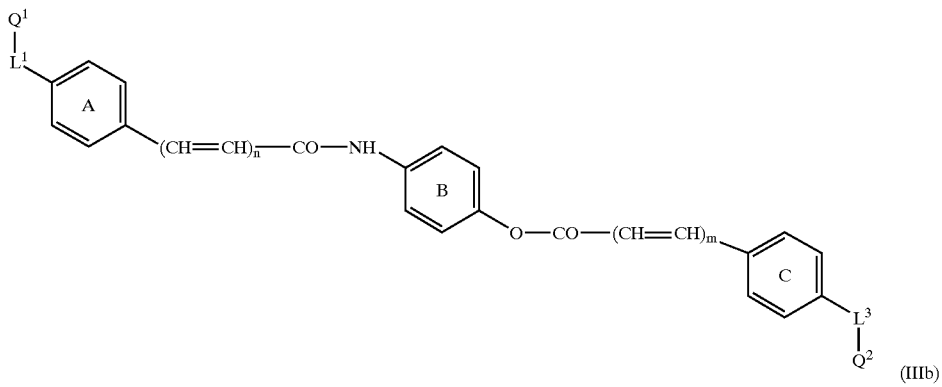

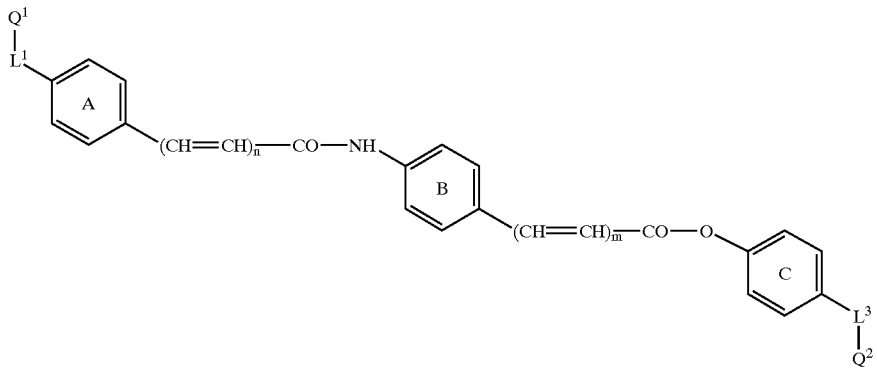

in which each of Q¹ and Q² independently is a polymerizable group; each of L¹ and L³ independently is a divalent linking group; each of n and m independently is 0 or 1; and each of the benzene rings A, B an C can have a substituent group.

20. An optically anisotropic element comprising a transparent support and a liquid crystal layer formed by polymerization of a polymerizable liquid crystal compound, wherein the polymerizable liquid crystal compound is represented by the formula (IIIa) or (IIIb):

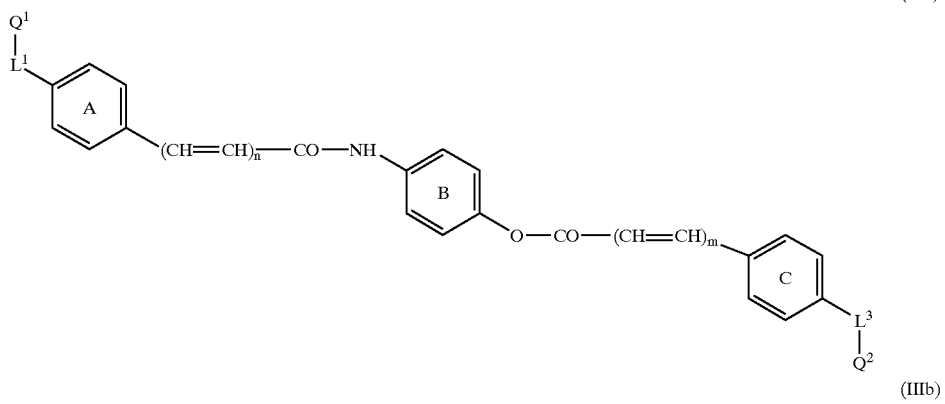
(IIIa)
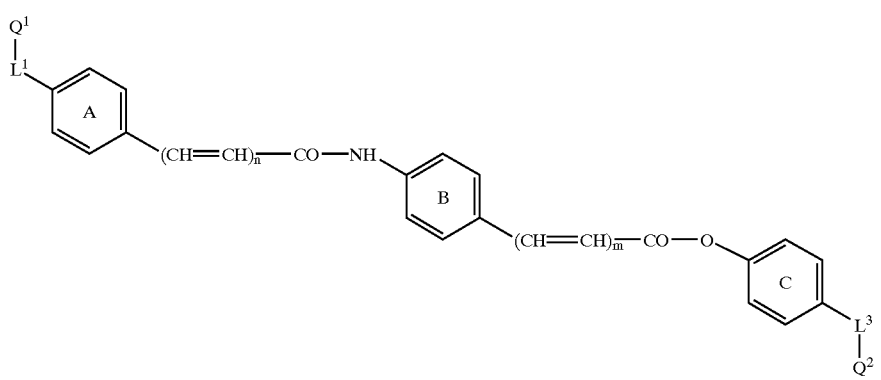
(IIIb)
in which each of $Q^1$ and $Q^2$ independently is a polymerizable group; each of $L^1$ and $L^3$ independently is a divalent linking group; each of n and m independently is 0 or 1; and each of the benzene rings A, B an C can have a substituent group.
* * * * *